(12) United States Patent
Strecker et al.

(10) Patent No.: US 9,533,936 B1
(45) Date of Patent: Jan. 3, 2017

(54) REMOVAL OF FATTY ACID FROM ESTERIFIED PROPOXYLATED GLYCERIN

(71) Applicant: Choco Finesse LLC, Indianapolis, MI (US)

(72) Inventors: Leopold Strecker, Warren, NJ (US); David Rowe, Indianapolis, IL (US); Dana Overman, Roswell, GA (US); Louie Flowers, Greenville, NC (US); Aaron Milhouse, Neeses, SC (US); Chess Mizell, Sanford, MI (US)

(73) Assignee: CHOCO FINESSE LLC, Indianapolis, IN (US)

( * ) Notice: Subject to any disclaimer, the term of this patent is extended or adjusted under 35 U.S.C. 154(b) by 0 days.

(21) Appl. No.: 15/183,289

(22) Filed: Jun. 15, 2016

(51) Int. Cl.
| | |
|---|---|
| *C11B 3/00* | (2006.01) |
| *C07C 67/54* | (2006.01) |
| *A23D 9/007* | (2006.01) |
| *A23G 1/36* | (2006.01) |

(52) U.S. Cl.
CPC ............. *C07C 67/54* (2013.01); *A23D 9/007* (2013.01); *A23G 1/36* (2013.01); *A23V 2002/00* (2013.01)

(58) Field of Classification Search
CPC ............ A23D 9/007; A23G 1/36; C07C 67/54
USPC ........................................................ 554/175
See application file for complete search history.

(56) References Cited

U.S. PATENT DOCUMENTS

| | | |
|---|---|---|
| 4,298,622 A | 11/1981 | Singh |
| 4,983,329 A | 1/1991 | Cooper |
| 5,387,429 A | 2/1995 | Cooper |
| 5,399,729 A | 3/1995 | Cooper |
| 5,512,313 A | 4/1996 | Cooper |
| 5,571,935 A | 11/1996 | Sekula |
| 5,603,978 A | 2/1997 | White |
| 5,681,939 A | 10/1997 | Ferenz |
| 6,268,010 B1 | 7/2001 | Sekula |
| 8,354,551 B1 | 1/2013 | Strecker |

FOREIGN PATENT DOCUMENTS

WO    9803461    1/1998

OTHER PUBLICATIONS

Cassidy; Minimizing Process Contaminants in Edible Oils, Inform, Mar. 2016, vol. 27 (3), pp. 6-11.

*Primary Examiner* — Deborah D Carr
(74) *Attorney, Agent, or Firm* — RatnerPrestia

(57) ABSTRACT

An esterified propoxylated glycerin process is improved by the incorporation of a vacuum distillation step whereby unreacted fatty acids are removed in a form suitable for direct reuse in a further esterification. The esterified propoxylated glycerin produced is low in color and has a low content of free fatty acid, making it suitable for use as a reduced calorie fat substitute in various food products.

21 Claims, No Drawings

REMOVAL OF FATTY ACID FROM ESTERIFIED PROPOXYLATED GLYCERIN

FIELD OF THE INVENTION

This invention pertains to methods for removing unreacted fatty acids from an esterified propoxylated glycerin reaction product, wherein degradation of the esterified propoxylated glycerin is reduced or eliminated and the fatty acids may be recovered in a form suitable for recycling for direct use in a further esterification process.

DISCUSSION OF THE RELATED ART

Esterified propoxylated glycerin has long been recognized as a substance potentially useful as a reduced calorie substitute for conventional triglyceride fats and oils in food compositions. However, to be fully acceptable for commercial use as a food ingredient, an esterified propoxylated glycerin must meet a number of significant criteria. For example, the esterified propoxylated glycerin should be low in both color and free fatty acid content. At the same time, however, any process employed to produce such an esterified propoxylated glycerin must also be relatively efficient and low in cost for the esterified propoxylated glycerin to be competitive with other fat substitutes on the market.

Esterified propoxylated glycerin may be prepared by esterification of propoxylated glycerin using fatty acid. In order to achieve essentially complete esterification of the propoxylated glycerin within a commercially practical period of time, it will generally be necessary to employ a slight excess of fatty acid (i.e., a molar amount of fatty acid that is greater than the quantity theoretically needed to convert all the hydroxyl end-groups of the propoxylated glycerin to ester groups). The reaction product thereby obtained contains unreacted fatty acid, which may affect the stability and/or organoleptic qualities of the product. For example, shorter chain fatty acids may impart a "soapy" or "pungent" taste and odor and free fatty acids are generally more susceptible to oxidation than their esterified counterparts. The presence of free fatty acid may also increase the rate of hydrolysis in food systems. A frying medium containing significant amounts of free fatty acids is typically characterized by the generation of an acrid odor and fumes during frying; moreover, the fried food thereby produced will generally have an off-taste.

In the past, steam distillation (steam stripping) has generally been employed to reduce the levels of free fatty acid in esterified propoxylated glycerin products. See, for example, U.S. Pat. No. 8,354,551. While this technique is effective, it has now been found that steam distillation under at least certain conditions may lead to partial hydrolysis of the esterified propoxylated glycerin component, thereby producing some amount of undesirable mono- and di-esterified propoxylated glycerin in admixture with fully esterified propoxylated glycerin. Additionally, if not carefully controlled, steam distillation may result in color development in the esterified propoxylated glycerin. Another disadvantage of steam distillation is that the fatty acids which are recovered are admixed with a significant quantity of water (steam condensate), which should be substantially removed in order for the recovered fatty acid to be suitable for reuse in a further esterification reaction. Such required further processing of the recovered fatty acid contributes to increasing the overall cost of operating a commercial scale esterified propoxylated glycerin production facility.

It has also recently been reported (Cassiday, "Minimizing process contaminants in edible oils," Inform, March 2016, Vol. 27 (3), pp. 6-11) that 3-MCPD esters and glycidyl esters can be formed in edible oils during standard deodorization conditions due to prolonged exposure to high temperatures.

In view of the foregoing, the development of improved methods for removing and recovering unreacted fatty acid from esterified propoxylated glycerin products would be advantageous.

SUMMARY OF THE INVENTION

The present invention provides vacuum distillation processes which avoid steam stripping and yet are remarkably effective in removing unreacted fatty acid from esterified propoxylated glycerin reaction products, while avoiding or reducing degradation or discoloration of the esterified propoxylated glycerin. The present invention enables the recovery of unreacted fatty acid in a form suitable for direct recycle into a propoxylated glycerin esterification.

Various exemplary aspects of the present invention may be summarized as follows:

Aspect 1: A method of refining an esterified propoxylated glycerin product comprised of esterified propoxylated glycerin and unreacted fatty acid, comprising subjecting the esterified propoxylated glycerin product to conditions whereby at least a portion of the unreacted fatty acid is volatilized under vacuum in the absence of added water and separated from a liquid phase comprised of the esterified propoxylated glycerin.

Aspect 2: The method of Aspect 1, wherein the esterified propoxylated glycerin product is heated at a temperature of from about 200° C. to about 300° C.

Aspect 3: The method of Aspect 1, wherein the esterified propoxylated glycerin product is heated at a temperature of from about 220° C. to about 280° C.

Aspect 4: The method of any one of Aspects 1-3, wherein the esterified propoxylated glycerin product is subjected to a pressure of not more than about 1 mm Hg.

Aspect 5: The method of any one of Aspects 1-3, wherein the esterified propoxylated glycerin product is subjected to a pressure of not more than about 0.1 mm Hg.

Aspect 6: The method of any one of Aspects 1-5, wherein the esterified propoxylated glycerin product is subjected to said conditions for less than about 5 minutes.

Aspect 7: The method of Aspect 1, wherein the esterified propoxylated glycerin product is subjected to a pressure of not more than about 1 mm Hg at a temperature of from about 220° C. to about 280° C.

Aspect 8: The method of Aspect 1, wherein the esterified propoxylated glycerin product is subjected to a pressure of not more than about 0.1 mm Hg at a temperature of from about 220° C. to about 280° C.

Aspect 9: The method of any one of Aspects 1-8, wherein a thin liquid film of the esterified propoxylated glycerin product is formed on a heated surface under vacuum.

Aspect 10: The method of any one of Aspects 1-9, wherein the method is carried out in a centrifugal still.

Aspect 11: The method of Aspect 10, wherein the centrifugal still comprises a heated rotating disk and the esterified propoxylated glycerin product has a residence time on the heated rotating disk of less than about 5 seconds.

Aspect 12: The method of Aspect 10 or 11, wherein the centrifugal still comprises a heated rotating disk and the heated rotating disk is maintained at a temperature of from about 220° C. to about 280° C.

Aspect 13: The method of any one of Aspects 10-12, wherein the centrifugal still comprises a vacuum chamber and the vacuum chamber is maintained at a pressure of less than about 1 mm Hg.

Aspect 14: The method of Aspect 10, wherein the centrifugal still comprises a heated rotating disk maintained at a temperature of from about 240° C. to about 270° C. and a vacuum chamber maintained at a pressure of less than about 0.1 mm Hg, the esterified propoxylated glycerin product having a residence time on the heated rotating disk of less than about 5 seconds.

Aspect 15: The method of any one of Aspects 1-9, wherein the method is carried out in a wiped or falling film evaporator.

Aspect 16: The method of any one of Aspects 1-15, wherein the liquid phase obtained following separation of at least a portion of the unreacted fatty acid comprises no more than 0.5 weight % free fatty acid, calculated as oleic acid.

Aspect 17: The method of any one of Aspects 1-16, wherein the esterified propoxylated glycerin product initially is comprised of from about 1 to about 20 weight % unreacted fatty acid, calculated as oleic acid.

Aspect 18: The method of any one of Aspects 1-17, wherein the esterified propoxylated glycerin product is obtained by reacting propoxylated glycerin with an excess of fatty acid.

Aspect 19: The method of any one of Aspects 1-18, wherein the esterified propoxylated glycerin product has been subjected to a bleaching step prior to separation of the unreacted fatty acid.

Aspect 20: The method of any one of Aspects 1-19, wherein unreacted fatty acid separated from the liquid phase is recycled for use in esterifying propoxylated glycerin to produce esterified propoxylated glycerin.

Aspect 21: The method of any one of Aspects 1-19, wherein unreacted fatty acid separated from the liquid phase is directly recycled for use, without further refinement or purification, in esterifying propoxylated glycerin to produce esterified propoxylated glycerin.

DETAILED DESCRIPTION OF CERTAIN EMBODIMENTS OF THE INVENTION

The esterified propoxylated glycerin product to be treated in accordance with the present invention may be prepared using any suitable method, but typically is obtained by reacting a propoxylated glycerin with an excess of one or more fatty acids under conditions effective to achieve substantially complete esterification of the hydroxyl groups of the propoxylated glycerin and to provide a product containing unreacted fatty acid.

The propoxylated glycerin reactant employed may be prepared by any of the standard methods known in the art such as, for example, the base-catalyzed reaction of propylene oxide with glycerin. While the molar ratio of propylene oxide to glycerin is not critical, in one embodiment of the invention from 2 to 20 moles of epoxide is reacted per mole of glycerin. In another embodiment, the propoxylated glycerin contains an average of 4 to 6 oxypropylene groups derived from propylene oxide. The propoxylation of glycerin can be carried out by the addition of propylene oxide to glycerin in the presence of a catalytic amount of an alkali metal alkoxylate at a temperature of from about 70° C. to 130° C. The alkali metal alkoxylate is desirably prepared by heating an alkali metal compound such as sodium hydroxide or potassium hydroxide with glycerin at an elevated temperature while continuously removing water, preferably under reduced pressure. In one embodiment, sufficient catalyst is present during propoxylation to provide an alkali metal content of about 0.0003 moles to 3.3 moles alkali metal per 100 g of glycerin. The propylene oxide may be fed incrementally into a reactor containing the glycerin and catalyst at a rate sufficient to maintain a pressure within the reactor of about 40 to 80 psia. The degree of propoxylation is controlled, and thus the molecular weight of the propoxylated glycerin as well, by regulating the amount of propylene oxide fed to the reactor. After the desired molecular weight is reached, the alkali metal may be removed prior to esterification by any suitable method such as absorption, ion exchange, or extraction. Propoxylated glycerin is also commercially available from multiple sources.

The fatty acids which may be employed as reactants in the esterification of the propoxylated glycerin may be saturated or unsaturated fatty acids or mixtures thereof. Straight chain as well as branched fatty acids may be used. In one embodiment, the fatty acid is a $C_{10}$-$C_{24}$ fatty acid (i.e., an acid which contains from 10 to 24 carbon atoms). Mixtures of different length fatty acids may be used. The fatty acid may be a monocarboxylic acid and/or a polycarboxylic acid (for example, a dimer or trimer fatty acid), although monocarboxylic acids are generally preferred. An excess of fatty acid, such as from 0.5 to 40% or 1 to 15% or 1 to 10% or 1 to 5% molar excess relative to the amount of propoxylated glycerin, is employed in order to catalyze the desired esterification such that the desired esterified propoxylated glycerin product may be rapidly obtained without adding other catalysts. The process may be advantageously performed with not more than 5%, or not more than 10%, or not more than 15% molar excess fatty acid.

Illustrative of the $C_{10}$-$C_{24}$ fatty acids which may be utilized are saturated acids such as capric, lauric, myristic, pentadecanoic, palmitic, heptadecanoic, stearic, nonadecanoic, eicosanoic, and behenic acid. Unsaturated fatty acids which are suitable for use include, but are not limited to, palmitoleic, oleic, linoleic, linolenic, and arachidonic acid. The mixtures of fatty acids which are conveniently available by conventional splitting (hydrolysis) of natural and hydrogenated vegetable oils and animal fats are also appropriate for use such as, for example, soybean oil fatty acids, hydrogenated high erucic rapeseed oil fatty acids, coconut oil fatty acids and the like. Mixtures of the aforementioned saturated and unsaturated fatty acids may be employed.

In one aspect of the invention, the fatty acid or mixture of fatty acids selected for reaction with the propoxylated glycerin is selected to provide the fatty acid content (composition) desired in the final esterified propoxylated glycerin product. The physical properties and other characteristics of esterified propoxylated glycerin compositions may be varied and controlled by adjusting the types of fatty acid ester groups present in the esterified propoxylated glycerin. For example, the solid fat index (SFI) of an esterified propoxylated glycerin may generally be increased by reducing the proportion of unsaturated fatty acid ester groups present in the esterified propoxylated glycerin. This may be achieved by esterifying a propoxylated glycerin with a fatty acid mixture containing unsaturated fatty acids and then hydrogenating the resulting esterified propoxylated glycerin to convert at least a portion of such unsaturated fatty acid ester groups to saturated fatty acid ester groups. Alternatively, a hydrogenation step is avoided by utilizing a fatty acid reactant during the esterification step that already possesses the desired final level of unsaturation.

The addition of distilled, highly concentrated, specific fatty acids is also beneficial when it is necessary to supplement the fatty acid mixture with a specific acid to increase or decrease the melting point of the finished esterified propoxylated glycerin. Stearic and behenic acids increase melting point while unsaturated fatty acid such as oleic or shorter carbon chain saturated acids (e.g., myristic or lauric) decrease the melting temperature of finished esterified propoxylated glycerins.

Esterification of propoxylated glycerin with a stoichiometric excess of one or more fatty acids to provide an initial esterification reaction mixture may be carried out for a time and at a temperature effective to achieve at least 95% esterification of the propoxylated glycerin, thereby providing an initial esterification reaction mixture. The direct esterification methods described in U.S. Pat. Nos. 5,681,939 and 8,354,551 (each of which is incorporated herein by reference in its entirety for all purposes) may, for example, be adapted for use in the esterification step. In such a direct esterification, propoxylated glycerin is esterified with excess fatty acid by a process wherein the temperature is increased incrementally and the pressure is reduced incrementally during the course of esterification while removing the water formed as a by-product. The propoxylated glycerin and the fatty acid may be introduced into a reaction zone to form a reaction mixture. The component reactants may be added separately or, if so desired, first combined or blended prior to entering the reaction zone. The reaction mixture may initially be at a temperature of from about 20° C. to about 80° C. and a pressure of from about 13 to 16 psia. The initial pressure, for example, may conveniently be atmospheric pressure and the initial temperature may be room temperature or, if needed to completely melt the reactants to form a homogeneous liquid phase, somewhat higher than room temperature. While the configuration and design of the reaction zone is not critical, a reactor vessel should be selected which is capable of heating and agitating (mixing) the contents of the vessel under subatmospheric pressure. Means for introducing the reactants and for removing the water of reaction (preferably, as an overhead stream in vapor form) from the vessel should also be provided. It may be advantageous to utilize equipment which will provide high shear mixing (e.g., a 5 to 600 m/min. tip speed, which typically may be achieved by a drive motor energy input of 1.5 to 3 kilowatts per 1000 liters of reaction mixture). Thin film reaction systems may also be employed. In a particularly desirable embodiment of the invention, no materials other than the fatty acid and the propoxylated glycerin are introduced into the reaction zone; i.e., no catalyst, solvent, entrainer, or azeotropic stripping agent is present.

The pressure may thereafter be reduced in an incremental manner within the reaction zone simultaneous with incrementally increasing the temperature of the reaction mixture. In one embodiment of the invention, the pressure is reduced below atmospheric pressure by the time the temperature of the reaction mixture exceeds 80° C. The reaction mixture may be agitated while removing from the reaction zone the water generated by esterification of the propoxylated glycerin by the fatty acid, preferably in vapor form as an overhead stream. Removal of the water has been found to be essential to driving the esterification, which is an equilibrium reaction, to the desired degree of completion. The rates at which the pressure and temperature are incrementally adjusted are preferably selected such that the desired level of esterification of the propoxylated glycerin is obtained within a practically short period of time (e.g., 12 hours or less) while minimizing losses of organic substances from the reaction zone. The rates at which pressure and temperature are varied may be constant or may, if so desired, be increased or decreased periodically. In one embodiment of the invention, for example, the rate of temperature increase is fairly high during the first 1-2 hours of the reaction while the rate of pressure decrease is relatively low during such period. The present invention is capable of being operated such that less than 5% (preferably, less than 1%) of the fatty acid which is initially charged to the reaction zone is lost during the course of esterification. In one embodiment, the molar ratio of water to fatty acid being removed from the reaction zone is at least 10:1. The optimum reaction parameters will vary somewhat depending upon such factors as the amount of excess fatty acid and the relative reactivities and volatilities of the fatty acid and propoxylated glycerin reactants, but may be readily determined by routine experimentation.

The esterification step of the process may be performed in a batch, continuous, or semi-continuous manner. When operated in a batch mode, for example, the initial reactants may be simply combined in a single vessel and then subjected to the temperature and pressure regimen described hereinabove such that the entire contents of the vessel are exposed simultaneously to the same reaction conditions. In a continuous process, the fatty acid and propoxylated glycerin may be introduced at one end of a reactor under the initial temperature and pressure conditions set forth above and then carried forward through the reactor in a series of stages or the like wherein the temperature is incrementally increased and the pressure is incrementally lowered in each successive stage, with the esterified propoxylated glycerin product being withdrawn from the other end of the reactor. Means are provided within each stage for withdrawing water vapor from the reaction mixture. A multiple stage continuous stirred tank reactor battery or cascade comprising two or more separate reactors or a multiple stage continuous stirred tank in a single shell may be utilized, for example.

The temperature of the reaction mixture is gradually increased through the course of the process until a final temperature not exceeding 275° C. is attained. In a preferred embodiment, the final temperature does not exceed 260° C. since some degradation of the reactants and/or esterified propoxylated glycerin may take place at higher temperatures. The final temperature may be at least 120° C. higher (in another embodiment, at least 150° C. higher) than the initial temperature. A final pressure of 4 psia or less (i.e., 0-4 psia) has been found to be helpful to drive the esterification reaction to a desirably high level of completion in a practically short period of time. Generally, it will be advantageous to esterify at least 95% (in another embodiment, at least 97%) of the available hydroxyl groups of the propoxylated glycerin. To rapidly attain such a high level of esterification, it will also be advantageous for the final temperature to be at least 200° C. The reaction mixture can be maintained at the final temperature and pressure for such time as may be needed to achieve the desired degree of esterification; depending upon the final temperature and pressure selected, this time may vary from as little as 1 minute to as long as 4 to 6 hours or longer. The total time required for esterification, as measured from the time variation of the pressure and temperature is initiated, will typically be from 4 to 15 hours.

Once the desired degree of esterification has been accomplished, the initial esterification reaction mixture may be contacted with a bleaching clay for a time and at a temperature effective to reduce the color of the initial esterification reaction mixture. The bleaching step not only improves color but also removes trace metals (detrimental to esterified propoxylated glycerin stability), residual phosphorus compounds (from phospholipids), propylene oxide, potassium and allyl alcohol that in trace levels may carry over from propoxylation of glycerin. The bleaching clay employed may be any of the bleaching clays known in the art to be suitable for use in the processing of conventional oils and fats. Bleaching clays may also be referred to as bleaching earths or bleaching adsorbents and may be based on various types of clays such as hormite, smectite, attapulgite, montmorillonite or mixtures thereof. Different classes of bleaching clays may be utilized in the bleaching step of the present invention, including, without limitation, the class of highly-active, mostly montmorillonite-based bleaching earths (also referred to in the art as High Performance Bleaching Earths, such as acid-activated montmorillonites), the class of naturally active clays (also known in the art as Natural Active Bleaching Earths) such as Fuller's earths, as well as the class referred to as surface activated systems or Surface Modified Bleaching Earths (which are typically prepared by subjecting a naturally active crude clay such as an attapulgite- and hormite-containing crude clay to a small quantity of acid. The bleaching clay may be in particulate or finely divided form and may have a relatively high surface area.

The quantity of bleaching earth employed will vary depending upon the activity of the particular bleaching clay selected as well as the amount of colored impurities in the initial reaction mixture to be bleached, among other factors. Typically, however, from about 0.5 to about 5% by weight bleaching clay, based on the weight of the reaction mixture, is used. The bleaching conditions will also be dependent upon the particular bleaching clay selected and the amount of bleaching clay, among other factors, but generally it will be advantageous to contact the bleaching clay with the reaction mixture at an elevated temperature (e.g., from about 80 to about 125° C.) while the reaction mixture is being maintained under a vacuum (e.g., a pressure of from about 10 to about 100 Torr). An acid such as phosphoric acid (e.g., in an amount of from about 0.05 to about 0.15% by weight) may also be combined with the esterified propoxylated glycerin prior to bleaching. Optionally, one or more of an activated carbon or a filter-aid may also be present. Contact times of from about 10 minutes to about 2 hours will generally be suitable. The bleaching step is advantageously carried out in the absence of molecular oxygen; for this reason, air should be rigorously excluded while the esterified propoxylated glycerin is being contacted with the bleaching clay.

Once bleaching is completed, the initial esterification reaction mixture is then filtered to remove the bleaching clay (and activated carbon, if present). A filter aid such as diatomaceous earth may be added to the mixture to facilitate filtration.

In one embodiment of the invention, the initial esterification reaction mixture is passed through a bed of bleaching clay (the bed may optionally also contain activated carbon, in particular activated carbon in granular form). The bed may be maintained at a suitable elevated temperature to promote color removal and/or to reduce the viscosity of the initial esterification reaction mixture. Multiple passes through the bed may be carried out in order to achieve the desired level of color reduction. In this embodiment of the invention, the bleaching earth contacting step and filtration step may be considered to be taking place concurrently.

Following the optional bleaching earth treatment step, the initial esterification reaction mixture (which may typically contain from about 1% to about 20% by weight free fatty acid, calculated as oleic acid) is subjected to vacuum distillation conditions effective to remove at least a portion of the unreacted fatty acid to provide an esterified propoxylated glycerin having a reduced level of free fatty acid. Preferably, such conditions involve molecular distillation, wherein very low pressures are maintained (e.g., less than about 1 mm Hg, less than about 0.1 mm Hg or even less than about 0.01 mm Hg). The esterified propoxylated glycerin product should be heated to a temperature sufficiently high so as to be effective in achieving volatilization of the unreacted fatty acid, but not exceeding a temperature at which the esterified propoxylated glycerin component of the product also volatilizes to a significant extent or begins to degrade or discolor. Such temperatures will depend upon the pressure selected and the characteristics of the particular unreacted fatty acids that are present in the esterified propoxylated glycerin product, but will generally be, in various embodiments of the invention, at least about 200° C., at least about 210° C., at least about 220° C., at least about 230° C., at least about 240° C. or at least about 250° C. and not more than about 300° C., not more than about 290° C., not more than about 280° C., or not more than about 270° C. Exemplary distillation temperatures may be from about 240° C. to about 280° C., from about 250° C. to about 270° C., or from about 255° C. to about 265° C. The lower the pressure, the lower the temperature which will be needed to effect volatilization and distillation of the unreacted fatty acid. It will be desirable to select temperature, pressure and residence (heating) conditions which are effective to remove most of the unreacted fatty acid (e.g., at least about 50%, at least about 60%, at least about 70%, at least about 80%, at least about 90%, or at least about 95% by weight of the unreacted fatty acid initially present in the esterified propoxylated glycerin product) while minimizing the amount of color developed in the esterified propoxylated glycerin thereby obtained. In various embodiments of the invention, the concentration of unreacted fatty acid in the esterified propoxylated glycerin following distillation is less than about 0.5%, less than about 0.4%, less than about 0.3%, less than about 0.2%, less than about 0.1%, less than about 0.08%, less than about 0.05% or less than about 0.03% by weight, calculated as oleic acid.

Especially suitable for use in the present invention are short path distillation techniques, in particular methods wherein a thin film of the esterified propoxylated glycerin product is maintained on a heated surface while under vacuum (reduced pressure). The film of the esterified propoxylated glycerin product may be, for example, from about 0.001 to about 0.05 mm in thickness. The film may be subjected to agitation while being heated under vacuum, in one embodiment of the invention.

Centrifugal stills are particularly preferred for use in the present invention. Centrifugal stills are well known in the art and are available from commercial suppliers such as Myers Vacuum (Kittanning, PA). In a centrifugal still, a feed material (in this case, an esterified propoxylated glycerin product containing one or more unreacted fatty acids as impurities, is introduced (by pumping, for example) into the proximity of the center of a heated rotating disk housed in a vacuum chamber. Prior to being deposited on the heated rotating disk, the esterified propoxylated glycerin may be subjected to one or both of a pre-heating step or a degassing step, to remove dissolved gasses and highly volatile substances). The feed material is spread by centrifugal force in a thin film (typically, about 0.002 to about 0.03 mm). Lighter (more volatile) components (e.g., fatty acids, in the case of the present invention) evaporate under the low pressure conditions present in the vacuum chamber and condense on a condenser, such as an internal water-cooled condenser. The heavier unevaporated residue (e.g., esterified propoxylated glycerin having a reduced content of unreacted fatty acid) slides off the rotating disk into a collecting gutter. Both fractions may separately flow by gravity to discharge pumps and are transferred out of the still (to a distillate collector, in the case of the distilled fatty acid, or to a residue collector, in the case of the esterified propoxylated glycerin). If the collected esterified propoxylated glycerin collected still has an undesirably high content of unreacted fatty acid, it may be recycled back through the centrifugal still one or more additional times. Typically, the feed rate of the esterified propoxylated glycerin product to the centrifugal still is controlled so that under the still conditions selected the residence time on the heated rotating disk is less than about 5 seconds, less than about 4 seconds, less than about 3 seconds or less than about 2 seconds and only one pass through the centrifugal still is needed in order to achieve the desired level of residual unreacted fatty acid in the esterified propoxylated glycerin.

Other types of distillation apparatus may also be used, such as wiped film evaporators (sometimes also referred to as agitated film evaporators or agitated thin film evaporators) and falling film evaporators.

A wiped film evaporator typically comprises an upright cylindrical vessel with a vertical rotor shaft extending concentrically within the vessel. An inlet pipe supplies a liquid (in the case of the present invention, an esterified propoxylated glycerin product containing unreacted fatty acid) to be subjected to distillation to a distributor which spreads the liquid around the inner wall of the vessel near the top of the vessel. A series of wiper assemblies carried by the rotor shaft below the distributor serve for the creation of a thin (typically, 0.1-4 mm) liquid film on the vessel's inner wall, heating means being provided to heat the liquid film while the film is under vacuum. Rotation of the wiper assemblies results in agitation of the liquid film, thereby promoting evaporation of the unreacted fatty acid. The wiper assembles provide good heat and mass transfer efficiency, with control of film thickness and residence time. The film, while being forced into turbulent flow by wiper blades, progresses down the inside body wall of the vessel aided by gravity and possibly also slots or other openings in the wiper blades. The unreacted fatty acid distills from the esterified propoxylated glycerin and is collected by means of a condenser (either internal or external to the wiped film evaporator). The evaporator may include a vapor outlet (for removal of gases and/or evaporated fatty acid) and a liquid discharge (for removal of esterified propoxylated glycerin having a reduced content of unreacted fatty acid). The wiped film evaporator may be single stage or multistage (wherein, for example, a first stage is used for degassing and removal of relatively volatile components of the feedstock).

If desired or needed, the esterified propoxylated glycerin following distillation may be contacted with activated carbon for a time and at a temperature effective to reduce the color of the esterified propoxylated glycerin. Such carbon treatment may also assist in reducing remaining off-flavors or off-odors, if any, in the esterified propoxylated glycerin. The carbon may be any form of activated carbon available, and may for example be derived from wood, bituminous coal, lignite coal, coconut, bone char, or any other source. Typically, the carbon is in the form of granules, but other physical forms such as powders or bead activated carbon may also be employed. It will generally be advantageous to utilize an activated carbon which is highly porous and which has a high surface area (e.g., over 100 $m^2/g$, over 200 $m^2/g$, or over 300 $m^2/g$). The amount of activated carbon is selected to be sufficient to reduce the color of the esterified propoxylated glycerin and/or improve the flavor and/or odor of the esterified propoxylated glycerin to the desired extent. Typically, from about 0.005 to about 1% by weight activated carbon, relative to the weight of the esterified propoxylated glycerin, is suitable.

In general, the temperature of the esterified propoxylated glycerin may be somewhat elevated while it is being contacted with the activated carbon; for example, the contact temperature may be from about 40° C. to about 120° C. The esterified propoxylated glycerin/activated carbon mixture may be stirred or otherwise agitated during the contacting step, with the mixture being maintained under an inert atmosphere (e.g., under an $N_2$ atmosphere). In one embodiment of the invention, the esterified propoxylated glycerin is passed through a bed of activated carbon one or more times until the desired level of purity is achieved.

The carbon-treated product is filtered to remove the activated carbon to provide an esterified propoxylated glycerin having organoleptic properties suitable to permit the esterified propoxylated glycerin to be used as a fat substitute in food compositions. Such filtration may be facilitated by adding a filter aid such as diatomaceous earth to the esterified propoxylated glycerin/activated carbon mixture prior to filtration. If the esterified propoxylated glycerin is solid or highly viscous at room temperature, it will be advantageous to conduct the filtration at a somewhat elevated temperature (e.g., about 40° C. to about 100° C.). Filtration may be repeated if residual particles are still present in the esterified propoxylated glycerin after the first filtration.

In various embodiments of the invention, the esterified propoxylated glycerin may be combined with one or more antioxidants before and/or after distillation. Any of the antioxidants conventionally used in fats and oils may be employed. If the esterified propoxylated glycerin is to be used as an ingredient in the preparation of a foodstuff, it will be beneficial to utilize an antioxidant approved for such end use. The preferred antioxidants are so-called "natural" antioxidants, but synthetic antioxidants, such as butylated hydroxytoluene (BHT), butylated hydroxyanisole (BHA), tertiary-butylhydroquinone (TBHQ) or propyl gallates, may also be employed. Natural antioxidants include tocopherols, various cereal and seed extracts, such as extracts from sesame and oats, phospholipids, organic acids, and proteins. However, the most widely known and most likely used in crude or refined vegetable oils are tocopherols. The tocopherols most commonly used are actually mixtures of four tocopherols: alpha; beta; gamma; and delta. It has been customary in recent years to supplement natural antioxidants with the synthetic antioxidants, reducing or chelating agents, such as L-ascorbyl palmitate, erythorbic acid, or citric acid, with some indications of synergistic effects from the combination. In the present invention, it is acceptable to use either the natural antioxidants, particularly tocopherols, alone or in combination with synthetic antioxidants or the reducing or chelating agents. It is, of course, also acceptable to use synthetic antioxidants alone, i.e. not combined with any natural antioxidants. The amount of antioxidant in the final esterified propoxylated glycerin may be, for example, from about 0.05 to about 1% by weight based on the weight of the esterified propoxylated glycerin.

Esterified propoxylated glycerin compositions having a reduced content of free fatty acid and produced in accordance with the present invention can be incorporated either alone or in combination with another fat and/or fat substitute or mimetic, into any food composition, or used in conjunction with any edible material (including conventional triglyceride oils and fats). For example, the esterified propoxylated glycerin products can be employed as fat replacements in fat-containing edible emulsions comprising an oil phase and an aqueous phase, including those high in fat, such as margarines and salad dressings, and those high in water, such as low fat spreads. The esterified propoxylated glycerin compositions can be employed as full or partial fat substitutes in dairy, meat, nut, egg, and other food products having a high natural fat component, and in vegetable, cereal and other products having a low natural fat component. The esterified propoxylated glycerin products can be employed as ingredients for all types of leavened baked products and unleavened baked products, and as coatings or coating ingredients for the same types of products. The esterified propoxylated glycerin products can be employed as an ingredient or a coating for snack food products, as well as a frying oil or a frying oil ingredient for fried snacks. In addition, the esterified propoxylated glycerin products can be employed to form edible barrier layers, either on the exposed surfaces of foods or as internal barrier layers used to separate various portions of a food product, e.g., in frozen pizza, nut coatings, or as a barrier between a dessert filling and an outer edible shell in fruit filled cookies and the like.

Representative fat-containing food products which can contain, in addition to other food ingredients, esterified propoxylated glycerin compositions produced in accordance with this invention in full or partial replacement of natural or synthetic fat are frozen desserts, e.g., frozen novelties, ice cream, sherbet, ices, and milk shakes; salad dressings; mayonnaises and mustards; dairy and non-dairy cheese spreads; margarine, margarine substitutes and blends; flavored dips; flavored bread or biscuit spreads; filled dairy products such as filled cream and filled milk; frying fats and oils; cocoa butter replacements and blends; candy, especially fatty candies such as those containing peanut butter or chocolate; reformed and comminuted meats; meat substitutes and extenders; egg products and substitutes; nut products such as peanut butter and other nut spreads, vegetable and fruit products; pet foods; whipped toppings; compound coatings; coffee lighteners, liquid and dried; puddings and pie fillings; frostings and fillings; chewing gum; breakfast cereals; bakery products, e.g., cakes, breads, rolls, pastries, cookies, biscuits, and savory crackers; and mixes or ingredient premixes for any of these. The esterified propoxylated glycerin products obtained by practice of the invention described herein may also be employed in any flavor, nutrient, drug or functional additive delivery system.

Within this specification embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

In this example, a series of molecular distillations were carried out for the purpose of determining suitable conditions for the effective removal of free fatty acids from an esterified propoxylated glycerin. The feedstock for distillation was a previously prepared and purified esterified propoxylated glycerin of acceptable quality for use in food (no odor, bland flavor, PV=0.1, AV=4.4, MDP=37.8° C., Lovibond color (1") 2R/11Y and total tocopherol =877 ppm) spiked with 14% by weight of a fatty acid blend.

The following distillation parameters were used:
15" centrifugal still (Myers Vacuum)
Degassing vacuum, 72 to 73 mTorr
Rotor vacuum, 3 to 4 mTorr
Distillation temperatures, 200, 220, 240 and 260° C.
Flow rate constant for each temperature, 30 lbs./hr
The results obtained are shown in Table 1.

TABLE 1

|  | RESIDUE | | | | DISTILLATE | | | |
| --- | --- | --- | --- | --- | --- | --- | --- | --- |
| Distillation Temp. ° C. | 200 | 220 | 240 | 260 | 200 | 220 | 240 | 260 |
| FFA, % as oleic | 1.30 | 0.65 | 0.73 | 0.29 | 103 | 99 | 99 | 95 |
| Hydroxyl Value | 4.5 | 4.7 | 4.4 | 4.3 | | | | |
| Peroxide Value | 3.3 | 3.3 | 3.8 | 4.3 | | | | |
| Anisidine Value | 5.7 | 6.3 | 5.7 | 6.4 | | | | |
| Color, Lovibond, 1" tube Red/Yellow | 7.6/70 | 8.7/70 | 8.7/70 | 9.2/70 | 6.0/70 | 4.7/40 | 4.7/38 | 3.2/28 |
| Mettler Drop Point, ° C. | 38.7 | 38.5 | 38.5 | 38.8 | | | | |
| Fatty Acid Composition, % | | | | | | | | |
| C16:0 | 4.0 | 3.9 | 3.9 | 4.0 | 1.9 | 1.8 | 1.8 | 1.8 |
| C18:0 | 62.0 | 61.5 | 61.2 | 61.4 | 62.7 | 60.8 | 60.5 | 60.3 |
| C18:1 | 0.7 | 1.0 | 1.6 | 1.1 | 0.1 | 0.1 | 0.1 | 0.1 |
| C20:0 | 23.1 | 23.2 | 23.0 | 23.2 | 22.3 | 22.6 | 22.6 | 22.5 |

TABLE 1-continued

| | RESIDUE | | | | DISTILLATE | | | |
|---|---|---|---|---|---|---|---|---|
| C22:0 | 10.2 | 10.4 | 10.3 | 10.4 | 12.5 | 14.0 | 14.4 | 14.5 |
| Other | | | | | 0.5 | 0.7 | 0.6 | 0.8 |
| Total FA | 100 | 100 | 100 | 100 | 100 | 100 | 100 | 100 |
| Tocopherols, ppm | | | | | | | | |
| Alpha | 78 | 34 | 77 | 78 | | | | |
| Beta | 15 | 1 | 16 | 15 | | | | |
| Gamma | 110 | 42 | 84 | 76 | | | | |
| Delta | 50 | 23 | 35 | 28 | | | | |
| Total tocopherols | 253 | 100 | 212 | 197 | | | | |

The results showed that a distillation temperature of 260° C. under the processing conditions tested was most effective in achieving a low level of free fatty acid (<0.5% by weight, measured as oleic acid). At lower temperatures, substantial removal of free fatty acid was still achieved. All samples of the residual esterified propoxylated glycerin had higher oxidation values (PV, AV) than the starting material. This was the result of no cooling and no nitrogen protection during this trial.

Example 2

Additional tests were conducted to determine if an esterified propoxylated glycerin product stripped of unreacted fatty acid in a centrifugal still is fully deodorized and comparable to an esterified propoxylated glycerin deodorized using steam stripping in sensory attributes. Further objectives of these tests were to verify the optimum distillation temperature and the effect of double pass (i.e., passing the esterified propoxylated glycerin through the centrifugal still twice) on sensory acceptance. The esterified propoxylated glycerin feedstock used was a laboratory-synthesized esterified propoxylated glycerin having a composition making it suitable for use in confectionary (chocolate) applications; the feedstock had been bleached using bleaching clay, but still had a free fatty acid content of 10.4% by weight calculated as oleic acid.

The following distillation parameters were used:
15" centrifugal still (Myers Vacuum)
Degassing vacuum, 72 to 73 mTorr
Rotor vacuum, 3 to 4 mTorr
Distillation temperatures, 260 and 270° C.
Cooling and $N_2$ protection of residue exiting the still
Table 2 shows the results obtained.

TABLE 2

| Sample designation | A | B | C | D | E | F |
|---|---|---|---|---|---|---|
| Distillation temperature, ° C. | Deodorized by steam stripping | 260 | 260 | 270 | 260 | 270 |
| Number of passes | n/a | single | single and deodorized by steam stripping | single | double | double |
| FFA, % as oleic | 0.19 | 0.20 | 0.20 | 0.22 | 0.18 | 0.13 |
| Hydroxyl Value | 4.6 | 3.0 | 3.1 | 3.0 | 3.0 | 3.0 |
| Peroxide Value | 0.7 | 0.9 | 0.7 | 1.0 | 1.2 | 1.4 |
| Anisidine Value | 3.3 | 3.0 | 4.8 | 1.4 | 1.0 | 2.9 |
| Lovibond color, 5.25" tube, Red/Yellow | 2.7/20 | 3.5/24 | 3.7/30 | 2.7/22 | 2.1/16 | 2.0/14 |
| Mettler Drop Point, ° C. | 38.4 | 38.7 | 38.7 | 38.8 | 38.6 | 38.7 |
| Tocopherols, ppm | | | | | | |
| Alpha | 202 | 23 | 8 | 6 | 14 | 4 |
| Beta | 24 | 3 | 3 | 2 | 0 | 0 |
| Gamma | 600 | 39 | 18 | 16 | 1 | 1 |
| Delta | 193 | 12 | 5 | 5 | 1 | 1 |
| Total tocopherols | 1010 | 77 | 34 | 29 | 16 | 6 |
| Sensory attributes in compound chocolate | | | | | | |
| Flavor, taste | Standard, acceptable | Standard, acceptable | Neutral, acceptable | Stronger, Sl. Chemical | Stronger, Sl. Chemical | Stronger, Sl. Chemical |

TABLE 2-continued

| Sample designation | A | B | C | D | E | F |
|---|---|---|---|---|---|---|
| Odor | Standard, acceptable | Standard, acceptable | Standard, acceptable | Strong off-odor | Strong off-odor | Strong off-odor |
| Color, visual | Good, golden, acceptable | Good, golden, acceptable | Good, golden, acceptable | Good, golden, acceptable | Good, golden, acceptable | Good, golden, acceptable |

All conditions tested resulted in a finished esterified propoxylated glycerin product having light color, a low content of free fatty acid and acceptable oxidative values. Control sample A (lab processed), sample B (single pass at 260° C.) and sample C (single pass at 260° C., followed by lab deodorization) showed comparable sensory attributes. A sensory panel judged all of these samples acceptable. Double pass samples and samples processed at 270° C. were judged inferior in taste and odor.

Example 3

Additional tests were conducted to determine if the processing conditions identified as preferred in Example 2 could be successfully scaled up. The esterified propoxylated glycerin feedstock used was a crude esterified propoxylated glycerin made by a commercial-scale esterification of propoxylated glycerin and having a composition making it suitable for use in confectionary (chocolate) applications; the feedstock had been bleached using bleaching clay and activated carbon, but still had a free fatty acid content of 10.6% by weight calculated as oleic acid.

The following distillation parameters were used:
36" centrifugal still (Myers Vacuum)
Degassing vacuum, 2.0 Torr
Rotor vacuum, 5.0 mTorr
Distillation temperature, 260° C.
Cooling and $N_2$ protection of residue exiting the still
Table 3 shows the results obtained.

TABLE 3

| Sample source | Drum 1 | Drum 11 | Drum 17 | Drum 21 |
|---|---|---|---|---|
| FFA, % as oleic | 0.05 | 0.05 | 0.05 | 0.06 |
| Peroxide Value | | | | |
| Anisidine Value | | | | |
| Lovibond color, 5.25" tube, Red/Yellow | 1.7/11 | 1.6/11 | 1.7/11 | 1.8/11 |
| Mettler Drop Point, ° C. | 39.0 | 39.1 | 38.5 | 38.7 |
| Fatty Acid Composition, % | | | | |
| C16:0 | 7.1 | 6.6 | 6.3 | 6.2 |
| C18:0 | 60.8 | 59.7 | 58.6 | 58.2 |
| C20:0 | 20.3 | 21.0 | 21.5 | 21.7 |
| C22:0 | 11.1 | 12 | 13 | 13.6 |
| Other | 0.7 | 0.7 | 0.6 | 0.3 |
| Total FA | 100 | 100 | 100 | 100 |
| Solid fat content - SFC | | | | |
| @ 10° C. | 97.1 | 97.4 | 97.4 | 97.4 |
| @ 20° C. | 96.0 | 96.2 | 96.1 | 96.1 |
| @ 25° C. | 94.6 | 94.9 | 94.8 | 94.8 |
| @ 30° C. | 89.8 | 90.1 | 89.7 | 89.6 |
| @ 35° C. | 43.3 | 43.7 | 44.7 | 44.0 |
| @ 40° C. | 0 | 0 | 0 | 0 |
| Tocopherols, ppm (added after stripping) | | | | |
| Alpha | 96 | 92 | 93 | 97 |
| Beta | 14 | 12 | 12 | 11 |
| Gamma | 506 | 499 | 506 | 519 |
| Delta | 198 | 197 | 200 | 206 |
| Total tocopherols | 814 | 800 | 811 | 833 |

These results show that the 36" centrifugal still performed as projected from the experiments using a 15" centrifugal still. The esterified propoxylated glycerin produced exhibited the lightest color and the lowest free fatty acid content, reflecting high quality. Comparable quality is not achievable in standard steam-refining deodorization. Very consistent product was achieved throughout the entire 40-hour continuous production run.

Example 4

This example demonstrates the feasibility of using a wiped film evaporator to effectively reduce the content of free fatty acid in an esterified propoxylated glycerin composition, without significant degradation of the product.

Feedstock for distillation: An esterified propoxylated glycerin containing 10-12% by weight free fatty acid (fatty acid content: palmitic acid 2.1%, stearic acid 61.5%, arachidic acid 15.0%, behenic acid 20.8%, other acids 0.6%).

Distillation Parameters: 3 temperatures tested, vacuum 6 mTorr, throughput rates 320 to 1002 g/hr.

Wiped Film Evaporator: Pope Scientific Inc. (laboratory scale, 2" glass still)

The esterified propoxylated glycerin products obtained following distillation were characterized as shown in Table 4. The products were comparable to lab steam-refined deodorized product (FFA 0.43% by weight calculated as oleic acid, Hydroxyl Value 2.0, no odor).

TABLE 4

| Distillation Temperature | 220° C. | 240° C. | 260° C. | 260° C. Sample A | 260° C. Sample B | 260° C. Sample C |
|---|---|---|---|---|---|---|
| Throughput rate, g/hr | 320 | 367 | 343 | 642 | 755 | 1002 |
| Hydroxyl Value, mg KOH/g | 2.42 | 2.34 | 2.19 | 2.27 | 2.29 | 2.45 |
| FFA % (as oleic) | 0.17 | 0.14 | 0.08 | 0.17 | 0.24 | 0.32 |
| Mettler Drop point, ° C. | 40.4 | 40.5 | 40.3 | 40.4 | 40.3 | 40.4 |
| DSC melting point, ° C. | 31.6 | 32.6 | 31.2 | 31.7 | 31.8 | 31.7 |
| Odor, sensory | none | none | none | none | none | none |

What is claimed is:

1. A method of refining an esterified propoxylated glycerin product comprised of esterified propoxylated glycerin and unreacted fatty acid, comprising subjecting the esterified propoxylated glycerin product to conditions whereby at least a portion of the unreacted fatty acid is volatilized under vacuum in the absence of added water and separated from a liquid phase comprised of the esterified propoxylated glycerin.

2. The method of claim 1, wherein the esterified propoxylated glycerin product is heated at a temperature of from about 200° C. to about 300° C.

3. The method of claim 1, wherein the esterified propoxylated glycerin product is heated at a temperature of from about 220° C. to about 280° C.

4. The method of claim 1, wherein the esterified propoxylated glycerin product is subjected to a pressure of not more than about 1 mm Hg.

5. The method of claim 1, wherein the esterified propoxylated glycerin product is subjected to a pressure of not more than about 0.1 mm Hg.

6. The method of claim 1, wherein the esterified propoxylated glycerin product is subjected to said conditions for less than about 5 minutes.

7. The method of claim 1, wherein the esterified propoxylated glycerin product is subjected to a pressure of not more than about 1 mm Hg at a temperature of from about 220° C. to about 280° C.

8. The method of claim 1, wherein the esterified propoxylated glycerin product is subjected to a pressure of not more than about 0.1 mm Hg at a temperature of from about 240° C. to about 270° C.

9. The method of claim 1, wherein a thin liquid film of the esterified propoxylated glycerin product is formed on a heated surface under vacuum.

10. The method of claim 1, wherein the method is carried out in a centrifugal still.

11. The method of claim 10, wherein the centrifugal still comprises a heated rotating disk and the esterified propoxylated glycerin product has a residence time on the heated rotating disk of less than about 5 seconds.

12. The method of claim 10, wherein the centrifugal still comprises a heated rotating disk and the heated rotating disk is maintained at a temperature of from about 220° C. to about 280° C.

13. The method of claim 10, wherein the centrifugal still comprises a vacuum chamber and the vacuum chamber is maintained at a pressure of less than about 1 mm Hg.

14. The method of claim 10, wherein the centrifugal still comprises a heated rotating disk maintained at a temperature of from about 240° C. to about 270° C. and a vacuum chamber maintained at a pressure of less than about 0.1 mm Hg, the esterified propoxylated glycerin product having a residence time on the heated rotating disk of less than about 5 seconds.

15. The method of claim 1, wherein the method is carried out in a wiped or falling film evaporator.

16. The method of claim 1, wherein the liquid phase obtained following separation of at least a portion of the unreacted fatty acid comprises no more than 0.5 weight % free fatty acid, calculated as oleic acid.

17. The method of claim 1, wherein the esterified propoxylated glycerin product initially is comprised of from 1 to about 20 weight % unreacted fatty acid, calculated as oleic acid.

18. The method of claim 1, wherein the esterified propoxylated glycerin product is obtained by reacting propoxylated glycerin with an excess of fatty acid.

19. The method of claim 1, wherein the esterified propoxylated glycerin product has been subjected to a bleaching step prior to separation of the unreacted fatty acid.

20. The method of claim 1, wherein unreacted fatty acid separated from the liquid phase is recycled for use in esterifying propoxylated glycerin to produce esterified propoxylated glycerin.

21. The method of claim 1, wherein unreacted fatty acid separated from the liquid phase is directly recycled for use, without further refinement or purification, in esterifying propoxylated glycerin to produce esterified propoxylated glycerin.

* * * * *

UNITED STATES PATENT AND TRADEMARK OFFICE
CERTIFICATE OF CORRECTION

PATENT NO. : 9,533,936 B1  
APPLICATION NO. : 15/183289  
DATED : January 3, 2017  
INVENTOR(S) : Leopold Strecker et al.

Page 1 of 1

It is certified that error appears in the above-identified patent and that said Letters Patent is hereby corrected as shown below:

On the Title Page

Item (71) Applicant should read:  
Choco Finesse LLC, Indianapolis, IN (US)

Item (72) Inventors should read:  
David Rowe, Indianapolis, IN (US)

Signed and Sealed this  
Sixth Day of June, 2017

Michelle K. Lee  
*Director of the United States Patent and Trademark Office*